Figure 1:
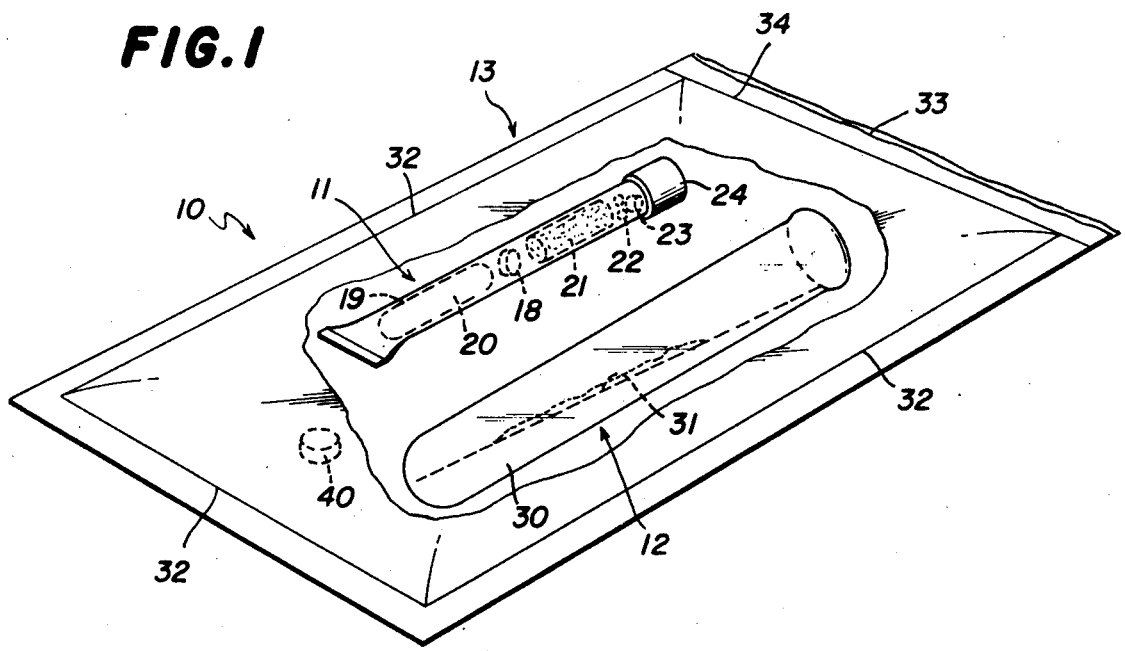

United States Patent [19]

Spinner et al.

[11] 4,013,422
[45] Mar. 22, 1977

[54] GAS GENERATING APPARATUS

[75] Inventors: Ernest Elliott Spinner, Grandview, Mo.; Melvin Wayne Hounsell, Beloit, Wis.

[73] Assignee: Marion Laboratories, Inc., Kansas City, Mo.

[22] Filed: Dec. 22, 1975

[21] Appl. No.: 643,259

[52] U.S. Cl. .................................................. 23/282
[51] Int. Cl.² .......................................... B01J 7/02
[58] Field of Search .............. 23/282; 195/109, 127

[56] References Cited

UNITED STATES PATENTS

| | | | |
|---|---|---|---|
| 3,100,692 | 8/1963 | Wachter | 206/84 X |
| 3,246,959 | 4/1966 | Brewer | 23/282 |
| 3,419,400 | 12/1968 | Hayhurst et al. | 23/282 X |
| 3,448,011 | 6/1969 | Russomanno | 195/142 X |
| 3,483,089 | 12/1969 | Brewer | 195/127 |
| 3,615,252 | 10/1971 | Di Pietro | 23/282 |
| 3,890,102 | 6/1975 | Gathmann et al. | 23/282 |

*Primary Examiner*—Joseph Scovronek
*Attorney, Agent, or Firm*—Merriam, Marshall, Shapiro & Klose

[57] ABSTRACT

A gas generating apparatus, for use in microorganism maintenance during sample transport, storage or incubation, comprising a container having an opening, a gas generating solid material in the container, an ampoule containing a liquid which is reactive with the solid material to produce a gas, said ampoule being openable from outside the container to free the liquid to contact the solid material, and means in the container which prevents liquid from flowing from the container after the ampoule is opened but which permits flow of gas generated in the container out of the container opening. A solid desiccant material may be put in the container to absorb water which may enter the container before the ampoule is opened, thereby preventing degradation or premature reaction of the gas generating solid material.

A reducing gas, such as hydrogen, is generated alone or with carbon dioxide. The hydrogen catalytically combines with oxygen to form an anaerobic atmosphere.

30 Claims, 2 Drawing Figures

U.S. Patent  Mar. 22, 1977  4,013,422

GAS GENERATING APPARATUS

This invention relates to disposable gas generating apparatus. More particularly, this invention is concerned with gas generating apparatus for use in collecting, transporting and storing bacterial cultures of the type which remain viable only when in the presence of a particular gaseous environment or atmosphere.

Many diseases of man and lower animals are bacterial in origin. The treatment of many bacterial diseases requires that the infecting organism be identified. A drug known to be effective against the infecting organism can then be prescribed.

The identification of an infecting organism is generally by means of a culture obtained from the ill patient or animal. The culture is then transported to a laboratory for determination of the identity of the infecting organism. Such laboratories require highly trained microbiologists and elaborate, expensive equipment. Suitable testing laboratories, accordingly, are not always readily available. It therefore becomes necessary for the patient to visit or animal be taken to the laboratory where the culture can be obtained and put immediately into the test procedures or for the culture to be taken at location remote from the laboratory and then transported to the laboratory for testing.

While the collecting of a culture generally presents no difficulties, the storage and/or transportation of the culture to a testing laboratory under conditions which guarantee the culture will be viable and free of contamination upon arrival presents serious problems. Although contamination from other organisms can generally be avoided by suitable means, the maintenance of a viable culture often requires, in addition to a suitable nutrient medium, the storage and transportation of the culture in a particular gaseous environment which promotes its viability.

Since bacteria of the anaerobic type are known to require an oxygen-deficient or oxygen-free gaseous environment, it is obvious that the transportation of an anaerobic bacteria culture should be effected in an environment having no or little oxygen. Organisms which are obligate anaerobes, such as the bacilli of tetanus, gas-gangrene, botulinus and bacteroides, require the absence of oxygen for proper growth. Furthermore, there are other organisms which require special atmospheres for proper growth. Although this is generally known by bacteriologists, it is disclosed in Brewer U.S. Pat. No. 3,246,959.

The Brewer U.S. Pat. No. 3,246,959 discloses a gas-producing device for generating an atmosphere conducive for maintaining the viability of organisms which require a special non-toxic atmosphere. The patent shows the chemical generation of hydrogen, carbon dioxide and acetylene for the purpose of supplying a non-toxic atmosphere to a culture in a container. A platinized wire gauze in the container is heated by electricity for the purpose of completely reacting oxygen in the container. The patent does not say what the oxygen reacts with or what else is to be present in the container at that time.

Aronoff U.S. Pat. No. 3,773,035 and Patterson U.S. Pat. No. 3,750,646 each disclose culture collecting and transporting apparatus. The apparatus is used by collecting a culture on a swabbing tip and placing it in contact with a medium for sustaining the culture. The system of each patent is intended to maintain a carbon dioxide enriched atmosphere around the collected culture to promote its growth.

Although the prior art discloses culture collecting and transporting apparatus which provide a controlled gaseous atmosphere around a collected culture, there is a need for a convenient, efficient, low cost, disposable apparatus for generating a gas for use in controlling the atmosphere surrounding a collected bacterial culture during storage, transport or incubation of the culture.

According to the invention there is provided novel gas generating apparatus which includes a container having an opening, a gas generating solid material in the container, an ampoule containing a liquid which is reactive with the solid material to produce a gas, said ampoule being openable from outside the container to free the liquid to contact the solid material, and means in the container which prevents liquid from flowing from the container after the ampoule is opened but which permits flow of gas generated in the container out of the container opening.

A solid desiccant material may be included in the container to absorb water which may enter the container before the apparatus is used, thereby preventing degradation or premature reaction of the gas generating solid material, regardless of the gas or gases which are subsequently generated or produced by the apparatus. The invention, however, contemplates having a desiccant material present when carbon dioxide is the sole gas generated.

The gas generating solid material in the container may be a material which, when contacted with the liquid in the ampoule, produces (1) a reducing gas which combines catalytically with oxygen in the air to produce water or (2) carbon dioxide, or (3) a mixture of a reducing gas and carbon dioxide.

The reducing gas advisably produced is hydrogen although acetylene or some other reducing gas which does not have an adverse effect on bacteria could be generated.

A catalyst which will promote reaction between the reducing gas and oxygen in the air to produce water may also be included in the container; however, the catalyst may be positioned outside of the container where it can catalyze the reaction between these gases to thereby produce an oxygen-free or oxygen-deficient atmosphere.

In a particular embodiment of the invention the container may be a flexible polymeric tube, advisably closed at one end and having an opening at the other end. While the tube may be open at both ends this requires that two plug means be used adjacent each end of the ampoule to keep the liquid from flowing out of the tube when the ampoule is ruptured. While feasible, this only increases the cost and provides no advantage. The ampoule can fit snugly in the tube with the gas generating solid material located above the ampoule toward the tube open end. The ampoule is advisably one which can be opened by squeezing the tube to rupture or break the ampoule to release the liquid. The means to prevent flow of the liquid from the tube after the ampoule is opened may be positioned between the ampoule and the opening in the tube and it may take the form of an absorbent plug. The desiccant is advisably positioned between the ampoule and the opening in the tube and preferably is located between the absorbent plug and the tube opening.

Figure 2:
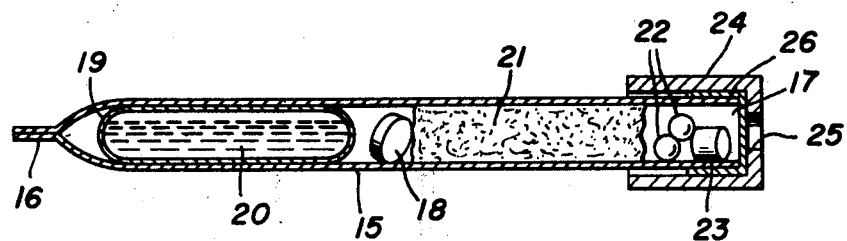

The invention will be described further in conjunction with the attached drawings, in which:

FIG. 1 is a perspective view of a package for transporting a bacteria culture and contains a gas generating apparatus provided by this invention; and FIG. 2 is a longitudinal, axial cross-sectional view of the gas generating apparatus shown in FIG. 1.

With reference to FIG. 1, the bacteria culture transporting package 10 constitutes a gas generating apparatus 11, and a test tube 12 containing a bacteria culture, both placed inside of a pouch or bag 13.

The gas generating apparatus 11 comprises a container in the form of an elongated plastic tube 15 which is closed at end 16 and is open at end 17. The tube 15 may be made of a flexible but self-supporting polymeric material such as polyethylene, polypropylene or a polyethylene-polypropylene copolymer such as the one available as Avisun 6011.

One or more gas generating solid tablets or pellets 18 is positioned in tube 15 above the ampoule 19. The tablet 18 has a composition which is suitable for generating a reducing gas such as hydrogen or acetylene, or carbon dioxide, or both a reducing gas and carbon dioxide.

Ampoule 19 is positioned in tube 15 more or less snugly so that it maintains its position. A liquid 20 is contained in ampoule 19. The composition of liquid 20 is selected so that it, when released from ampoule 19, will react with tablet 18 to generate one or more gases. The ampoule 19 can be made of glass or some other material which is nonreactive with liquid 20 or the components of gas generating tablet 18. The ampoule 19 is advisably made so that it will rupture or break upon application of finger pressure to the outside of tube 15 adjacent the ampoule wall. In this way the ampoule may be opened and the liquid 20 freed to react with tablet 18 which drops into the freed liquid.

A liquid absorbent plug 21, such as of polyester fibers, is positioned in tube 15 after the ampoule 19 is placed in the tube. The absorbent plug 21 is thus located between the ampoule 19 and the tube open end 17 so that liquid cannot flow from the tube. The plug 21 may be covered with a polytetrafluoroethylene-polypropylene laminate (Gore-Tex) which allows passage of gas at low pressure (7 psig) but not liquid.

One or more desiccant pellets 22 are positioned between liquid absorbent plug 21 and the open end 17 of the tube 15 as shown in FIG. 2. Any suitable desiccant or water dehydrating material can be used for this purpose although it is preferred to use molecular sieves. Nevertheless, magnesium sulfate or calcium chloride are representative of other desicant materials which may be used satisfactorily.

Also positioned between liquid absorbent plug 21 and the open end 17 of tube 15 is one or more catalyst pellets 23. The catalyst pellet 23 is provided to induce catalytic reaction between the reducing gas which is formed by the combination of liquid 20 with tablet 18 and any oxygen which may be in tube 15 or in any surrounding atmosphere in which the gas generating apparatus 11 may be placed. A 5% palladium-on-alumina catalyst may be used although other catalysts which induce the reaction at room temperature may be employed.

A polymeric cap 24 having a central hole 25 and a fibrous biological filter 26 is pressed firmly over the open end of tube 15. The filter 26 is made of a material which will permit gas generated in tube 15 to flow from the tube readily but which will remove any bacteria which may be possibly present in tube 15 and which might otherwise escape during the flow of gas from the tube.

The gas generating tablet 18 may have the following composition when it is desired to produce simultaneously both carbon dioxide and hydrogen as the reducing gas:

| | | |
|---|---|---|
| Potassium borohydride | 78 | mg. |
| Zinc | 78 | mg. |
| Sodium chloride | 90 | mg. |
| Sodium bicarbonate | 84 | mg. |
| Lactose DT | 164 | mg. |
| Microporous cellulose--Avicel PH102 | 150 | mg. |
| Tabletting lubricant--Calcium stearate | 6.0 | mg. |

If it is desired to produce only hydrogen and no carbon dioxide the sodium bicarbonate may be omitted from the composition set forth above for tablet 18. However, if it is desired to produce only carbon dioxide then the potassium borohydride, zinc and sodium chloride may be omitted.

The ampoule 19 may contain as the liquid 20, 1.1 ml. of 1.8 N hydrochloric acid in a glass ampoule 1-13/16 inches long. It should be understood, however, that the size of ampoule 19 and the strength and quantity of liquid 20 in the ampoule are coordinated with the ingredients of tablet 18 so as to result in the generation of a predetermined volume of one or more gases.

The dehydrating agent or desiccant 22 is advisably included in the gas generating apparatus to remove water and water vapor therefrom which may enter the tube through opening 17 during sterilization, such as by ethylene oxide gas sterilization, in the manufacturing process, or to remove water vapor which may penetrate the tube in one way or another. Removal of water in this way is desirable to preserve the stability of the gas generating tablet 18, although it is understood that under some conditions the desiccant may not be necessarily employed. According to the invention the desiccant 22 is included whenever it is intended to generate carbon dioxide by means of a tablet 18.

The described gas generating apparatus 11 constitutes a disposable throw-away unit which is intended to be employed only once for the production of carbon dioxide or a reducing gas or both such gases. It is particularly useful in culture collecting and transporting systems where it is considered advisable for an organism to remain viable to be surrounded by oxygen-free or low oxygen atmosphere. The gas generating apparatus is also highly useful for generating a carbon dioxide atmosphere for use in transporting or storing bacteria cultures which require, or are most likely to remain viable longer, when placed in an atmosphere containing a substantial amount more of carbon dioxide than is found in the atmosphere.

Although the gas generating apparatus illustrated by FIG. 2 may be used in many ways to generate special atmospheric environments, one such way in which it may be employed is illustrated by FIG. 1. A test tube 12 containing an agar slant 30 with an anaerobic organism 31 growing thereon is placed in plastic pouch or bag 13. The bag 13 may be made of plastic flexible film or sheet material of low gas permeability. The bag 13 may be made of two sheets of plastic film heat sealed 32 around three-side edges, thereby leaving an open mouth 33 through which the tube 12 may be inserted into the bag. The gas generating apparatus 11 is then inserted into bag 13 and the mouth 33 is sealed shut in any suitable way, such as by means of heat seal 34.

The resulting package is then put in vertical position with the cap 24 in top position. The ampoule 19 is then broken by squeezing tube 15. The acid in the ampoule 19 is thereby released and tablet 18 drops into contact with the acid. Reaction of the acid with the potassium borohydride causes hydrogen to be generated within the tube while reaction of the acid with the sodium bicarbonate results in the generation of carbon dioxide. Both of these gases flow through the entire length of tube 15 since plug 21 is gas permeable. Plug 21 absorbs excess acid and prevents it from flowing elsewhere in the tube. The liquid acid also combines with the ingredients of tablet 18 to form a slush which further serves to hold the liquid acid in place. The hydrogen intermixes with the oxygen in tube 15 and by means of the catalyst 23 these two gases react to form water, thereby scavenging oxygen from the internal space of tube 15. Oxygen from bag 13 also flows into tube 15 and is caused to react with the hydrogen by means of the catalyst 23.

The bag 13 may be made from a transport material of low gas permeability, such as polyester film (Mylar) laminate identified as No. CL5040 (Clear Lam Products). As the carbon dioxide and hydrogen are generated in tube 15 the gases flow out opening 17 through filter 26 into bag 13 which, if desired, may contain one or more catalyst pellets 40 like catalyst pellet 23. When catalyst pellet 40 is to be used it is unnecessary, even though advisable, to include the catalyst pellet 23 in the tube 15. The generated gases cause the bag 13 to balloon or expand outwardly. The ballooning effect is evidence that the gases have generated as expected. However, immediately upon generating of hydrogen one or both of the catalyst pellets 23 and 40 induces reaction of the hydrogen with the oxygen to form water. The described catalytic removal of oxygen from bag 13 does not significantly effect the ballooning immediately. However, some hours or so after the unit is activated the carbon dioxide may have penetrated the walls of bag 13 causing a vacuum to develop in the receptacle. The external atmospheric pressure then will press or collapse the flexible walls of the bag together. This condition may result even without oxygen entering the receptacle because the gas permeability of the wall material may permit preferential flow of carbon dioxide out of the bag but not oxygen in.

The chemical means suitable for generating the gaseous carbon dioxide in the apparatus of this invention is not to be limited to the specific embodiment set forth herein. Other well known chemical means for gaseous carbon dioxide generating may be used. Broadly, any solid material which upon contact with a liquid releases carbon dioxide in adequate amount in a reasonably short time may be used. The least expensive method, of course, is to contact a carbonate or bicarbonate salt with a dilute acid which will not produce vapors having an adverse effect on the culture. Instead of putting a dilute acid in the ampoule it can be filled with water, and sodium bicarbonate and citric acid, or some suitable acid salt, can be put in pellet 18 to generate carbon dioxide. Other feasible systems will appear readily to skilled chemists.

Although the above example illustrates the production of hydrogen as the reducing gas by the use of specific chemicals, i.e. potassium borohydride, zinc, sodium chloride and dilute hydrochloric acid, other solid materials can be used in conjunction with other liquids to produce hydrogen or some other reducing gas which will react catalytically with oxygen to remove it from the space around the culture. Thus, water alone can be plced in ampoule 19 and the solid pellet 18 can be formulated to contain a material which reacts with water safely and reasonably quickly to produce hydrogen. Thus, sodium borohydride, lithium aluminum hydride, lithium hydride, calcium hydride, aluminum hydride and lithium borohydride can be used since they react with water as well as aqueous acid to form hydrogen. Such hydrides also react with other liquids such as alcohols to form hydrogen so that sometimes it may be desirable to replace the water or acid with an alcohol, provided it does not adversely affect the culture. Hydrogen can, of course, be produced by the reaction of a metal such as iron, zinc, aluminum and magnesium with a suitable acid such as sulfuric acid and hydrochloric acid.

Instead of using hydrogen as the reducing gas to remove oxygen from the tube 15, it is feasible to form acetylene by the reaction of calcium carbide in pellet 18 and water or dilute acid in ampoule 19.

The foregoing detailed description has been given for clearness of understanding only, and no unnecessary limitations should be understood therefrom, as modifications will be obvious to those skilled in the art.

What is claimed is:

1. A gas generating apparatus comprising:
    a container having an opening,
    a gas generating solid material in the container,
    an ampoule containing a liquid which is reactive with the solid material to produce a gas, said ampoule being rupturable by squeezing the outside of the container to free the liquid to contact the solid material,
    means in the container which prevents liquid from flowing from the container after the ampoule is opened but which permits flow of gas generated in the container out of the container opening, and
    a solid desiccant material in the container which absorbs water which may enter the container before the ampoule is opened, thereby preventing degradation or premature reaction of the gas generating solid material.

2. A gas generating apparatus according to claim 1 in which the container opening is covered by a microbacteriological filter.

3. A gas generating apparatus according to claim 1 in which the container is an elongated flexible tube closed at one end and having an opening at the other end.

4. A gas generating apparatus according to claim 3 in which the ampoule fits snugly in the tube and the gas generating solid material is between the tube open end and the ampoule.

5. A gas generating apparatus according to claim 4 in which the means which prevents liquid flow is an absorbent plug located in the tube between the ampoule and the opening in the tube.

6. A gas generating apparatus according to claim 4 in which the desiccant is positioned between the ampoule and the opening in the tube.

7. A gas generating apparatus according to claim 5 in which the desiccant is positioned between the absorbent plug and the opening in the tube.

8. A gas generating apparatus according to claim 3 in which the tube has an open end covered by a cap having a hole permitting flow of gas from the tube.

9. A gas generating apparatus according to claim 8 in which the hole in the cap is covered by a microbacteriological filter.

10. A gas generating apparatus comprising:
   an elongated flexible tube having an opening at one end,
   a reducing gas generating solid material in the tube,
   an ampoule in the tube containing a liquid which is reactive with the solid material to produce a reducing gas catalytically reactive with oxygen at room temperature, said ampoule being rupturable by squeezing the outside of the tube to free the liquid to contact the solid material, and
   means in the tube which prevents liquid from flowing from the tube after the ampoule is opened but which permits flow of the reducing gas generated in the tube out of the opening.

11. A gas generating apparatus according to claim 10 in which the tube is closed at one end and the tube contains a solid desiccant material which absorbs water which may enter the tube before the ampoule is opened, thereby preventing degradation or premature reaction of the gas generating solid material.

12. A gas generating apparatus according to claim 10 in which the solid material produces hydrogen.

13. A gas generating apparatus according to claim 10 in which the tube opening is covered by a microbacteriological filter.

14. A gas generating apparatus according to claim 12 in which the tube contains a desiccant and a catalyst which induces reaction of generated hydrogen with oxygen in the air to produce water.

15. A gas generating apparatus according to claim 14 in which the ampoule fits snugly in the tube and the gas generating solid material is between the tube open end and the ampoule.

16. A gas generating apparatus according to claim 15 in which the means which prevents flow is an absorbent plug located in the tube between the ampoule and the opening in the tube.

17. A gas generating apparatus comprising:
   a container having an opening,
   gas generating solid material in the container,
   an ampoule containing a liquid which is reactive with the solid material to simultaneously produce carbon dioxide and hydrogen, said ampoule being ruturable by squeezing the outside of the container to free the liquid to contact the solid material, and
   means in the container which prevents liquid from flowing from the container after the ampoule is opened but which permits flow of carbon dioxide and hydrogen generated in the container out of the container opening.

18. A gas generating apparatus according to claim 17 having a solid desiccant material in the container which absorbs water and which may enter the container before the ampoule is opened, thereby preventing degradation or premature reaction of the gas generating solid material.

19. A gas generating apparatus according to claim 17 in which the container contains a catalyst which induces reaction of the generated hydrogen with oxygen in the air to produce water.

20. A gas generating apparatus according to claim 17 in which the means which prevents liquid flow is an absorbent plug located in the tube between the ampoule and the opening in the tube.

21. A gas generating apparatus according to claim 17 in which the container is a tube having an open end covered by a cap having a hole permitting flow of gas from the tube, and the hole in the cap is covered by a microbacteriological filter.

22. A gas generating apparatus comprising:
   an elongated flexible tube closed at on end and having an opening at the other end,
   a hydrogen was generating solid material in the tube,
   an ampoule in the tube containing a liquid which is reactive with the solid material to produce hydrogen gas catalytically reactive with oxygen at room temperature, said ampoule being rupturable by squeezing the outside of the tube to free the liquid to contact the solid material,
   means in the tube which prevents liquid from flowing from the tube after the ampoule is opened but which permits flow of the hydrogen gas generated in the tube out of the opening,
   a catalyst in the tube which induces reaction of the generated hydrogen with oxygen in the air to produce water, and
   in the tube a solid desiccant material which absorbs water which may enter the tube before the ampoule is opened, thereby preventing degradation or premature reaction of the hydrogen generating solid material.

23. A gas generating apparatus according to claim 22 in which the means which prevents liquid flowing from the tube is an absorbent plug located in the tube between the ampoule and the opening in the tube.

24. A gas generating apparatus according to claim 22 in which the desiccant is positioned between the opening in the tube and the gas generating solid material.

25. A gas generating apparatus according to claim 22 in which the tube opening is covered by a microbacteriological filter.

26. A gas generating apparatus according to claim 23 in which the desiccant is positioned between the plug and the opening in the tube.

27. A gas generating apparatus comprising:
   an elongated flexible tube closed at one end and having an opening at the other end,
   gas generating solid material in the tube,
   an ampoule containing a liquid which is reactive with the solid material to simultaneously produce carbon dioxide and hydrogen, said ampoule being rupturable by squeezing the outside of the tube to free the liquid to contact the solid material, and
   means in the tube which prevents liquid from flowing from the tube after the ampoule is opened but which permits flow of the carbon dioxide and hydrogen generated in the tube out of the opening,
   a catalyst in the tube which induces reaction of the generated hydrogen with oxygen in the air to produce water, and
   in the tube a solid desiccant material which absorbs water which may enter the tube before the ampoule is opened, thereby preventing degradation or premature reaction of the gas generating solid material.

28. A gas generating apparatus according to claim 27 in which the means which prevents liquid flowing from the tube is an absorbent plug located in the tube between the ampoule and the opening in the tube.

29. A gas generating apparatus according to claim 27 in which the desiccant is positioned between the opening in the tube and the gas generating solid material.

30. A gas generating apparatus according to claim 27 in which the tube opening is covered by a microbacteriological filter.

* * * * *

UNITED STATES PATENT AND TRADEMARK OFFICE
CERTIFICATE OF CORRECTION

PATENT NO. : 4,013,422
DATED : March 22, 1977
INVENTOR(S) : Ernest Elliott Spinner and Melvin Wayne Hounsell It is certified that error appears in the above-identified patent and that said Letters Patent are hereby corrected as shown below:

Column 1, line 25, insert --a-- after "at"; column 4, line 48, insert --an-- after "by"; column 5, line 23, "transport" should be --transparent--; line 35, "generating" should be --generation--; line 53, "generating" should be --generation--; column 6, line 5, "plced" should be --placed--; column 8, line 5, "on" should be --one--; line 7, "was" should be --gas--

Signed and Sealed this

Seventeenth Day of May 1977

[SEAL]

Attest:

RUTH C. MASON
Attesting Officer

C. MARSHALL DANN
Commissioner of Patents and Trademarks